United States Patent
Miyazawa et al.

(10) Patent No.: US 8,269,031 B2
(45) Date of Patent: Sep. 18, 2012

(54) PHOSPHORYLCHOLINE GROUP-CONTAINING COMPOUND, METHOD OF MANUFACTURING A PHOSPHORYLCHOLINE GROUP-CONTAINING COMPOUND, SURFACE-MODIFYING AGENT, AND A METHOD OF MODIFYING A SURFACE USING A SURFACE-MODIFYING AGENT

(75) Inventors: Kazuyuki Miyazawa, Yokohama (JP); Yukimitsu Suda, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/287,530

(22) Filed: Nov. 2, 2011

(65) Prior Publication Data

US 2012/0059183 A1 Mar. 8, 2012

Related U.S. Application Data

(62) Division of application No. 12/521,788, filed on Jun. 30, 2009, now Pat. No. 8,222,443.

(30) Foreign Application Priority Data

Jan. 18, 2007 (JP) ................................ 2007-009482

(51) Int. Cl.
C07F 9/11 (2006.01)
(52) U.S. Cl. ....................................................... 558/87
(58) Field of Classification Search ........................ 558/87
See application file for complete search history.

(56) References Cited

U.S. PATENT DOCUMENTS

| 4,937,369 A | 6/1990 | Chapman et al. |
| 5,091,551 A | 2/1992 | Chapman et al. |
| 5,229,162 A | 7/1993 | Chapman et al. |
| 5,599,587 A | 2/1997 | Bowers et al. |
| 2003/0134420 A1 | 7/2003 | Lollo et al. |
| 2007/0241054 A1 | 10/2007 | Miyazawa et al. |
| 2008/0113942 A1 | 5/2008 | Suda et al. |

FOREIGN PATENT DOCUMENTS

| EP | 1690867 | 8/2006 |
| JP | 6-501697 | 2/1994 |
| JP | 6-065264 | 3/1994 |
| JP | 07-118123 | 5/1995 |
| JP | 09-003132 | 1/1997 |
| JP | 10-298240 | 11/1998 |
| JP | 2000-279512 | 10/2000 |
| JP | 2002-098676 | 4/2002 |
| JP | 2003-040942 | 2/2003 |
| JP | 2005-187456 | 7/2005 |
| JP | 2006-007203 | 1/2006 |
| JP | 3793546 | 7/2006 |

OTHER PUBLICATIONS

Peter Friedmana et al., Correlation of Antiphospholipid Antibody Recognition with the Structure of Synthetic Oxidized Phospholipids., Journal of Biological Chemistry, 2000, vol. 277, No. 9, p. 7010.
International Search Report mailed on Mar. 11, 2008.
Chinese Office Action mailed Nov. 23, 2011.

*Primary Examiner* — Joseph Kosack
(74) *Attorney, Agent, or Firm* — IPUSA, PLLC

(57) ABSTRACT

A phosphorylcholine group-containing compound that is a structure having a phosphorylcholine group represented by the following formula 1 and an amino group or a group derived from an amino group in an identical compound.

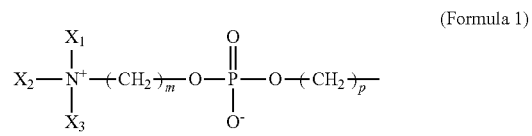

(Formula 1)

(In the formula, m is 2 or more and 6 or less and p is 1 or 2. Each of $X_1$, $X_2$ and $X_3$ is an alkyl group whose carbon number is 1 or more and 6 or less.)

1 Claim, 2 Drawing Sheets

PHOSPHORYLCHOLINE GROUP-CONTAINING COMPOUND, METHOD OF MANUFACTURING A PHOSPHORYLCHOLINE GROUP-CONTAINING COMPOUND, SURFACE-MODIFYING AGENT, AND A METHOD OF MODIFYING A SURFACE USING A SURFACE-MODIFYING AGENT

CROSS-REFERENCES TO RELATED APPLICATIONS

This application is a divisional application under 35 U.S.C. 121 of co-pending U.S. patent application Ser. No. 12/521,788 filed on Jun. 30, 2009, now U.S. Pat. No. 8,222,443, which claims the benefit of the priority based on Japanese Patent Application No. 2007-009482 filed on Jan. 18, 2007, the entire content of which is hereby incorporated by reference.

BACKGROUND OF THE INVENTION

1. Field of the Invention

The present invention relates to a phosphorylcholine group-containing compound, a method of manufacturing a phosphorylcholine group-containing compound, a surface-modifying agent, and a method of modifying a surface using a surface-modifying agent.

2. Description of the Related Art

Conventionally, a polymer of a compound having a phosphorylcholine group has been known as a biocompatible polymer and biocompatible materials in which various substrates are coated with this polymer have been developed.

Therefore, a method of utilizing a powder coated with a homopolymer and copolymer of 2-methcryloyloxyethylphosphorylcholine as a powder for cosmetic material to provide a cosmetic material with improved moisture retention and skin adhesion properties has been proposed (for example, see Japanese Patent Application Publication No. 07-118123). A medical material and separating medium coated with a polymer having a phosphorylicholine group have also been disclosed (for example, see Japanese Patent Application Publication No. 2000-279512 and Japanese Patent Application Publication No. 2002-098676).

Furthermore, the above-mentioned material is a polymer obtained by synthesizing a monomer having a phosphorylcholine structure and polymerizing it, wherein principally an acrylic monomer having a hydroxyl group and 2-chloro-1,3,2-dioxaphosphorane-2-oxide, and further trimethylamine are reacted to provide a quaternary ammonium.

For such a compound, a method for manufacturing a copolymer of 2-methecryloyloxyethylphosphorylcholine and a methacrylate ester is disclosed (for example, see Japanese Patent Application Publication No. 09-003132).

For a similar compound, a method for manufacturing a homopolymer of 2-methacryloyloxyethylphosphorylcholine is disclosed (for example, see Japanese Patent Application Publication No. 10-298240).

However, synthetic conditions are complex and there are problems in safety in regard to the above-mentioned methods for manufacturing a polymer having a phosphorylcholine group as disclosed in Japanese Patent Application Publication No. 07-118123, Japanese Patent Application Publication No. 2000-279512, Japanese Patent Application Publication No. 2002-098676, Japanese Patent Application Publication No. 09-003132, and Japanese Patent Application Publication No. 10-298240.

Furthermore, it is difficult to coat the entire surface of an object effectively, and even if a costing is made, there is a problem of its easy release from the object, in regard to a polymer having a phosphorylcholine group and method for coating and modifying a surface of an object with the polymer as disclosed in Japanese Patent Application Publication No. 07-118123, Japanese Patent Application Publication No. 2000-279512, Japanese Patent Application Publication No. 2002-098676, Japanese Patent Application Publication No. 09-003132, and Japanese Patent Application Publication No. 10-298240.

Moreover, the entire surface of an object is coated with a polymer having a phosphorylcholine group, and therefore, only the phosphorylcholine group is not necessarily exposed on the surface, depending on a steric structure which is allowed to have by the polymer. Therefore, there is a problem that a surface-modifying method having a complete biocompatibility is not necessarily provided.

SUMMARY OF THE INVENTION

One object of the present invention is to provide a phosphorylcholine group-containing compound that directly provides a desired amount of phosphorylcholine group to an object surface conveniently and with a high versatility.

Another object of the present invention is to provide a convenient and highly safe method of manufacturing a phosphorylcholine group-containing compound while a compound having a phosphorylcholine group preliminarily is a starting material.

Yet another object of the present invention is to provide a surface-modifying agent including a phosphorylcholine group-containing compound and a surface-modifying method using the surface-modifying agent including a phosphorylcholine group-containing compound.

According to one aspect of the present invention, there is provided a phosphorylcholine group-containing compound that is a structure having a phosphorylcholine group represented by the following formula 1 and an amino group or a group derived from an amino group in an identical compound.

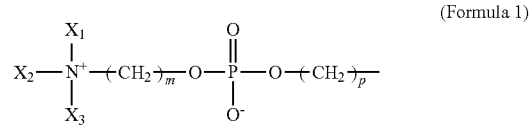

(Formula 1)

(In the formula, m is 2 or more and 6 or less and p is 1 or 2. Each of X1, X2 and X3 is an alkyl group whose carbon number is 1 or more and 6 or less.)

According to another aspect of the present invention, there is provided a phosphorylcholine group-containing compound that is a structure in which a phosphorylcholine group represented by the following formula 1 bonds to an amino group or a group derived from an amino group via a C—N linkage, an ester linkage or an amide linkage.

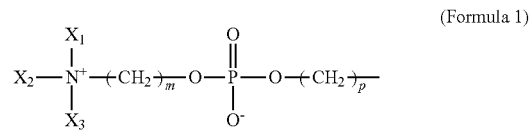

(Formula 1)

(In the formula, m is 2 or more and 6 or less and p is 1 or 2. Each of X1, X2 and X3 is an alkyl group whose carbon number is 1 or more and 6 or less.)

According to another aspect of the present invention, there is provided a phosphorylcholine group-containing compound represented by the following formula 2.

(Formula 2)

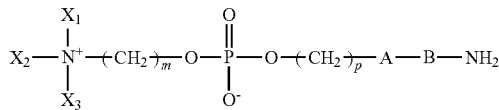

(In the formula, m is 2 or more and 6 or less and p is 1 or 2. Each of X1, X2 and X3 is an alkyl group whose carbon number is 1 or more and 6 or less. A is a secondary amine linkage, an ester linkage or an amide linkage. B is an alkyl group, a polyoxyethylene group, or an aromatic group.)

According to another aspect of the present invention, there is provided a method of manufacturing the phosphorylcholine group-containing compound as described above, wherein a phosphorylcholine group-containing compound in the manufacturing method is synthesized by means of an oxidative cleavage reaction of glycerophosphorylcholine to synthesize a phosphorylcholine derivative having an aldehyde group and a reductive amination reaction of a compound having an amino group or a group derived from an amino group and the phosphorylcholine derivative having an aldehyde group.

According to another aspect of the present invention, there is provided a method of manufacturing the phosphorylcholine group-containing compound as described above, wherein a phosphorylcholine group-containing compound in the manufacturing method is synthesized by means of an oxidative cleavage reaction of glycerophosphorylcholine to synthesize a phosphorylcholine derivative having a carboxyl group and a condensation reaction of a compound having an amino group or a group derived from an amino group and the phosphorylcholine derivative having a carboxyl group.

According to another aspect of the present invention, there is provided a surface-modifying agent including the phosphorylcholine group-containing compound as described above.

According to another aspect of the present invention, there is provided a method of modifying a surface using the surface-modifying agent including a phosphorylcholine group-containing compound as described above.

According to one aspect of the present invention, it is possible to provide a phosphorylcholine group-containing compound that directly provides a desired amount of phosphorylcholine group to an object surface conveniently and with a high versatility.

According to another aspect of the present invention, it is possible to provide a method of manufacturing a phosphorylcholine group-containing compound that directly provides a desired amount of phosphorylcholine group to an object surface conveniently and with a high versatility.

According to another aspect of the present invention, it is possible to provide a surface-modifying agent including a phosphorylcholine group-containing compound that directly provides a desired amount of phosphorylcholine group to an object surface conveniently and with a high versatility.

According to another aspect of the present invention, it is possible to provide a surface-modifying method using a surface-modifying agent including a phosphorylcholine group-containing compound that directly provides a desired amount of phosphorylcholine group to an object surface conveniently and with a high versatility.

DETAILED DESCRIPTION OF THE PREFERRED EMBODIMENTS

Figure 1:
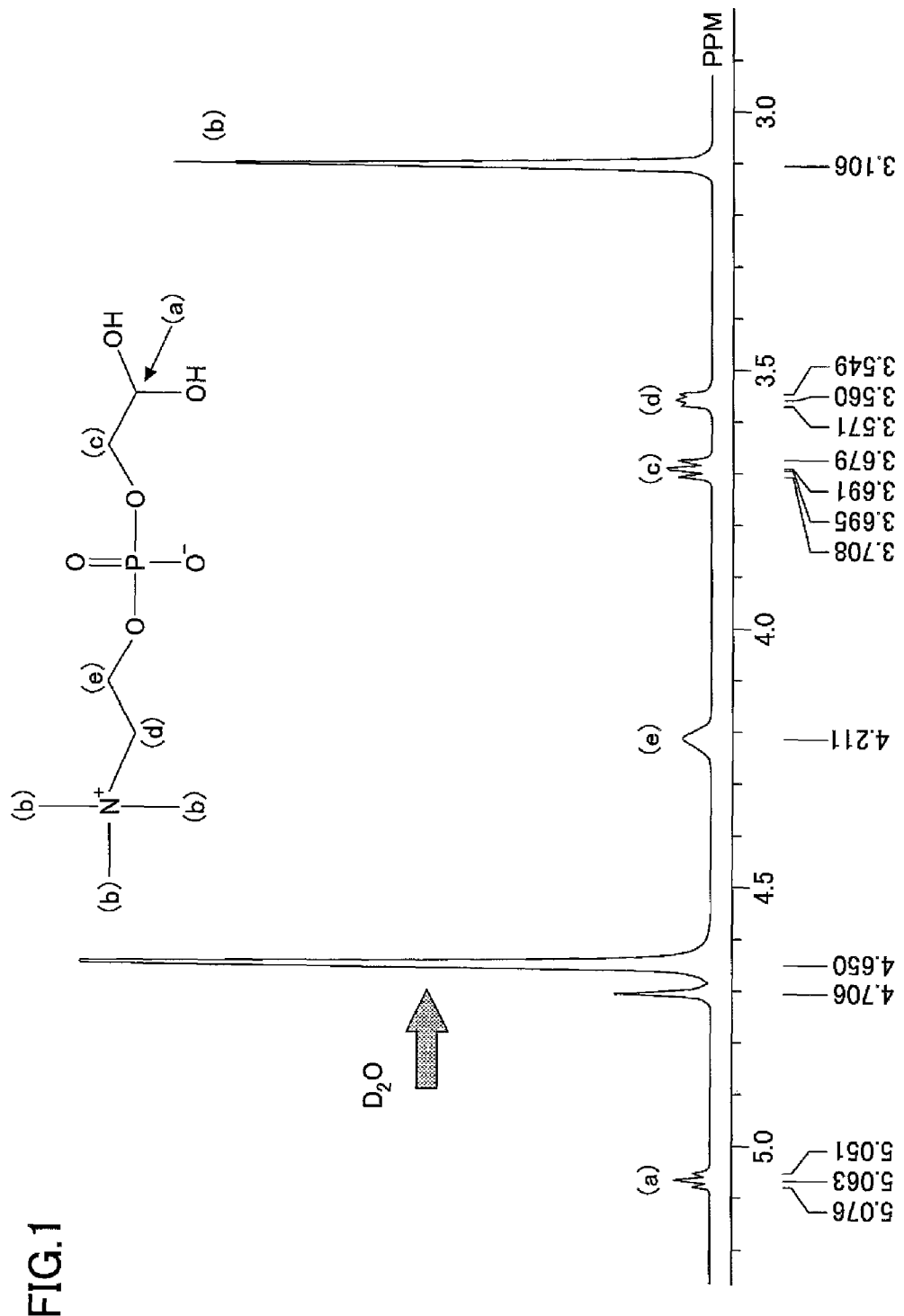
FIG. 1 is the structural formula of a phosphorylcholine derivative in practical example 1 of the present invention and its $^1$H-NMR spectrum in heavy water.

Next, the best mode of an embodiment of the present invention will be described.

Phosphorylcholine Group-Containing Compounds

It is possible to obtain a compound according to the present embodiment by directly reacting an amine compound containing a phosphorylcholine compound and an object having a functional group that reacts with the amine compound. Surface modification is possible whether these compounds are purified or non-purified, and it is possible to obtain an effect such as protein adsorption suppression. Furthermore, a phosphorylcholine group-containing compound represented by the following formula 3 is a new compound.

(Formula 3)

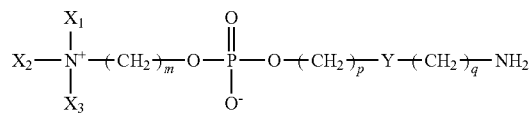

In the formula, m is 2 or more and 6 or less and p is 1 or 2. Each of X1, X2 and X3 is an alkyl group whose carbon number is 1 or more and 6 or less. A is a secondary amine linkage (—NH—), an ester linkage, or an amide linkage. B is an alkyl group, a polyoxyethylene group, or an aromatic group.

Methods for Manufacturing a Phosphorylcholine Group-Containing Compound of Formula 3

For example, when a phosphorylcholine group-containing compound is synthesized by means of a secondary amine linkage, a phosphorylcholine group-containing compound of formula 3 is synthesized by an oxidation reaction of glycerophosphorylcholine with periodic acid to synthesize a phosphorylcholine derivative having an aldehyde group and a condensation reaction of a compound having an amino group and the phosphorylcholine derivative having an aldehyde group as described above.

Alternatively, when a phosphorylcholine group-containing compound is synthesized by means of an amide linkage or an ester linkage, a phosphorylcholine group-containing compound of formula 3 is synthesized by an oxidation reaction of glycerophosphorylcholine with periodic acid and ruthenium trichloride to synthesize a phosphorylcholine derivative having a carboxyl group and a condensation reaction of a compound having an amino group and the phosphorylcholine derivative having a carboxyl group as described above.

Surface-Modifying Agents

A compound of formula 3 as described above is useful for a substance surface-modifying agent. That is, a substance surface is modified by introducing a desired amount of phosphorylcholine group thereinto. Furthermore, it is possible to conduct the introduction of a phosphorylcholine group into a substance surface by a convenient method.

For example, a conventional phosphorylcholine group-containing compound as disclosed in Japanese Patent No. 3793546 does not have an amino group but has a carboxyl group or the like at the terminal thereof. Therefore, when a substance surface is modified by the conventional phosphorylcholine group-containing compound, it is necessary to add an amino group to the substance surface preliminarily by means of a surface reaction due to plasma treatment, silicone gas-phase treatment, and the like. Because a phosphorylcholine group-containing compound according to the present embodiment has an amino group at a terminal at the opposite side of a phosphorylcholine group, it is possible to bond a functional group having a reactivity with an amino group, such as a carboxyl group on a substance surface. Therefore, pretreatment of a substance as described above is not needed.

For a specific modification method, in the case of a substance having a carboxyl group on a surface thereof, a chemical linkage (amide linkage) is formed by a dehydration reaction of a carboxyl group on the substance surface and an amino group of the compound of formula 3. This chemical reaction proceeds very easily and quantitatively in most organic solvents or water in a temperature range of 10 to 250° C. Due to the dehydration reaction, it is possible to conduct surface modification with a chemically and physically very stable phosphorylcholine group.

Alternatively, when a raw material has a group having reactivity with an amino group, such as an aldehyde group, an isocyanate group, an epoxy group, and an alkyl halide group on a surface thereof, it is possible to introduce a phosphorylcholine group similarly.

As described above, this bonding reaction involving dehydration has a property of proceeding quantitatively. By utilizing this property, the amount of a phosphorylcholine group-containing compound to be charged into a reaction system, a reaction temperature, a reaction time, and the like are set at predetermined conditions, whereby it is possible to provide a desired amount of phosphorylcholine group-containing compound bonding to a substance surface.

Blocking Agents for an Affinity Particle

The compound of formula 3 as described above is also useful as a blocking agent for an affinity particle. A desired amount of phosphorylcholine group is introduced into, for example, the surface of an agarose particle, which is a carrier for an affinity particle. Subsequently, an antibody is bound to the agarose particle to provide an affinity particle. When a predetermined protein is adsorbed by using the antibody on the affinity particle, a phosphorylcholine group-containing compound on the agarose particle is to inhibit (block) non-specific adsorption of a protein onto a surface of the agarose particle. Furthermore, it is possible to conduct introduction of a phosphorylcholine group into a surface of this substance by a convenient method, similarly to the case of a surface-modifying agent as described above.

For example, an affinity particle to which a conventional phosphorylcholine group-containing compound as disclosed in Japanese Patent Application Publication No. 2006-007203 bonds does not have an amino group but has an alkyl group or the like at a terminal thereof. Therefore, when a conventional phosphorylcholine group-containing compound is bonded to the surface of an agarose particle, it is necessary to add an amino group to a surface of this substance preliminarily by the treatment as described above. Because a phosphorylcholine group-containing compound according to the present embodiment has an amino group at a terminal at the opposite side of a phosphorylcholine group, it is possible to bond a functional group having reactivity with an amino group, such as a carboxyl group on the surface of an agarose particle. Therefore, pretreatment of a substance as described above is not needed.

Furthermore, because it is possible to bond to an agarose carrier directly, it is possible to bond a number of phosphorylcholine group-containing compounds to the surface of an agarose particle compactly, compared to the case of conducting amino group addition treatment as described above. Therefore, it is possible to secure a sufficient antibody bonding region while the surface of an agarose particle is not occupied by a blocking agent. Accordingly, an affinity particle in which a phosphorylcholine group-containing compound according to the present embodiment is a blocking agent is allowed to purify more target protein more specifically.

PRACTICAL EXAMPLES

An embodiment of the present invention will be described by practical examples in more detail below.

Practical Example 1

Method of Manufacturing a Phosphorylcholine Group-Containing Compound of Formula 3

A phosphorylcholine derivative represented by the following formula 4 is dissolved in distilled water. The phosphorylcholine derivative of the following formula 4 is a publicly-known compound and its commercial product is available.

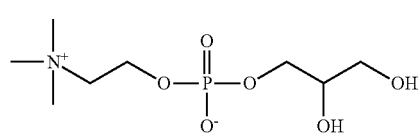

(Formula 4)

An aqueous solution of a compound of formula 4 is cooled in an ice-water bath, and addition of sodium periodate and agitation for 5 hours are conducted. A reaction fluid after the agitation is subjected to vacuum concentration and vacuum drying and a phosphorylcholine derivative having an aldehyde group represented by the following formula 5 is extracted with methanol.

(Formula 5)

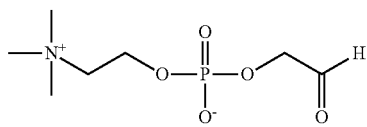

Then, 20 equivalent amounts of ethylenediamine are added into a solution of formula 5 in methanol. This mixture solution is agitated at room temperature for a predetermined time period and subsequently is cooled in ice. A suitable amount of sodium borohydride is added into this ice-cooled mixture solution, and return to room temperature and agitation for 16 hours are conducted. During this time period, dry nitrogen is kept flowing into a reactor. A precipitate of the reaction fluid after agitation is removed by means of filtration, and subsequently, vacuum concentration and vacuum drying are conducted to obtain a solution of formula 6 in methanol.

(Formula 6)

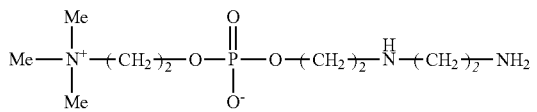

Confirmation of Synthesis of an Aldehyde Compound Containing a Phosphorylcholine Group 450 mg of L-α-glycerophosphorylcholine was dissolved in 15 ml of distilled water and cooling in ice-water bath was conducted. 750 mg of sodium periodate was added into the cooled aqueous solution and agitation was conducted for 5 hours. A reaction fluid after the agitation was subjected to vacuum concentration and vacuum drying and an objective substance was extracted with methanol.

FIG. 1 is the structural formula of a phosphorylcholine derivative in practical example 1 of the present invention and its $^1$H-NMR spectrum in heavy water.

When referring to FIG. 1, it is found that an objective compound of formula 5 is manufactured which is a phosphorylcholine derivative in which an aldehyde group is introduced at a terminal thereof.

(Formula 5)

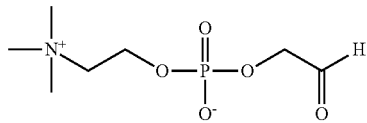

Practical Example 2

Method of Manufacturing a Phosphorylcholine Group-Containing Compound of Formula 3

An aqueous solution of the compound of formula 4 as described above was cooled in an ice-water bath, and addition of sodium periodate and ruthenium trichloride and agitation for 3 hours were conducted. For a reaction fluid after the agitation, addition of methanol and further agitation for 30 minutes are conducted. A precipitate of the reaction fluid after agitation is removed by means of filtration, and vacuum concentration and vacuum drying are conducted to obtain a phosphorylcholine derivative having a carboxyl group represented by the following formula 7.

(Formula 7)

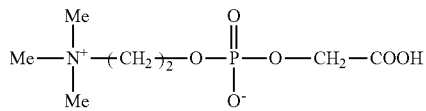

Then, 20 equivalent amounts of ethylenediamine are added into a solution of formula 7 in methanol. A suitable amount of triazine-type dehydration condensation agent (DMT-MM) is added into this mixture solution and agitation for 3 hours is conducted. After the agitation, a precipitate is removed by means of filtration, and vacuum concentration and vacuum drying are conducted to obtain a solution of the following formula 8 in methanol.

(Formula 8)

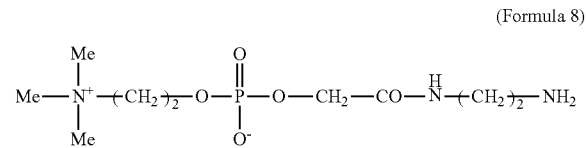

Confirmation of Synthesis of a Carboxyl Compound Containing a Phosphorylcholine Group 500 mg of L-α-glycerophosphorylcholine was dissolved in 10 ml of distilled water and cooling in an ice-water bath was conducted. 1700 mg of sodium periodate and 8 mg of ruthenium trichloride was added into the cooled aqueous solution and agitation was conducted at room temperature for 2 hours. A reaction fluid after the agitation was subjected to vacuum concentration and vacuum drying and an objective substance was extracted with methanol.

Figure 2:
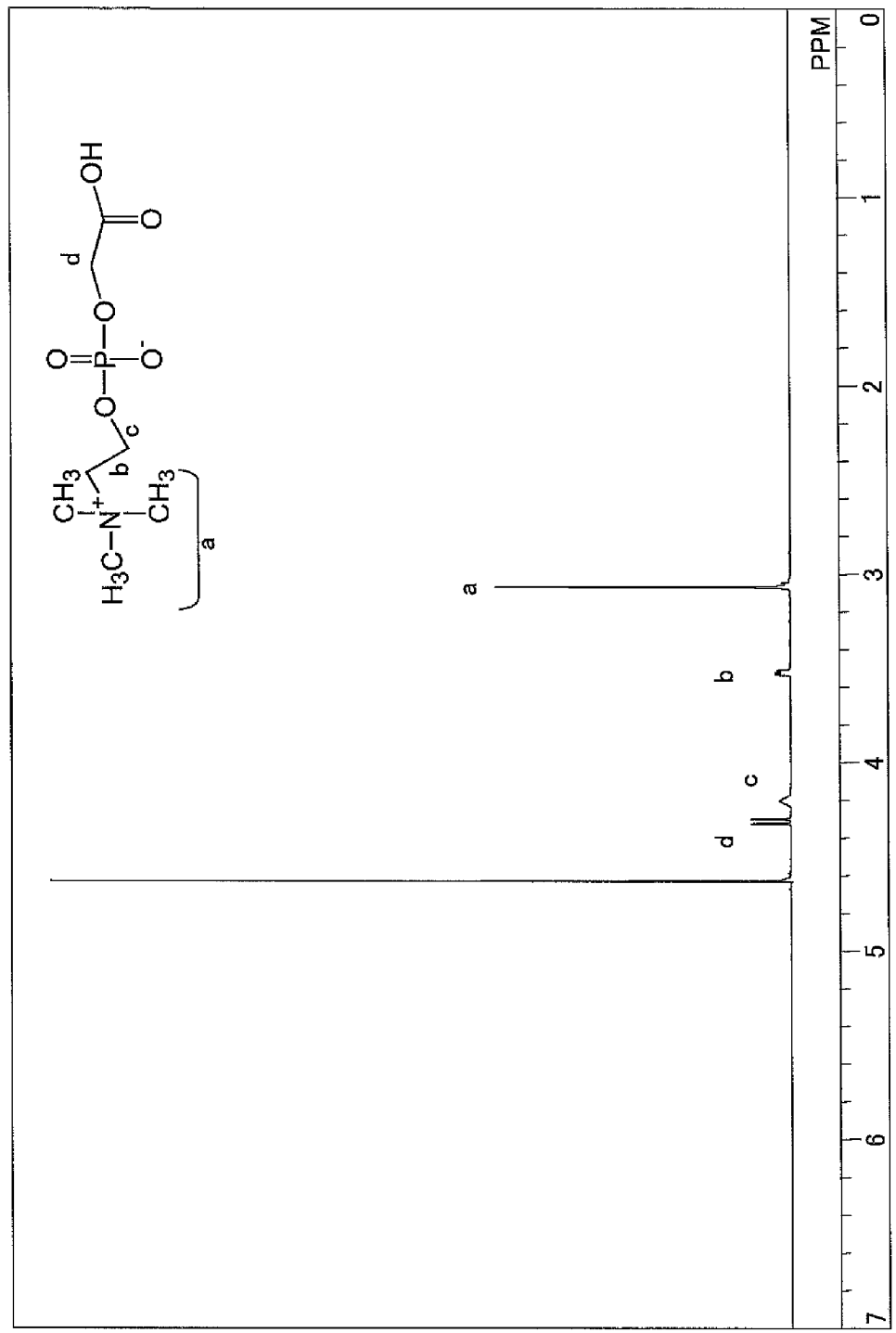
FIG. 2 is the structural formula of a phosphorylcholine derivative in practical example 2 of the present invention and its $^1$H-NMR spectrum in heavy water.

FIG. 2 is the structural formula of a phosphorylcholine derivative in practical example 2 of the present invention and its $^1$H-NMR spectrum in heavy water.

When referring to FIG. 2, it is found that an objective compound of formula 7 is manufactured which is a phosphorylcholine derivative in which a carboxyl group is introduced at a terminal thereof.

According to the present embodiment and practical examples, a phosphorylcholine group-containing compound having an amino group at a terminal thereof is provided, and therefore, it is possible to provide a desired and arbitrary amount of a phosphorylcholine group to surfaces of various objects by means of a one-step and very convenient reaction. As a result, it is possible to manufacture a raw material having a desired function attributed to a phosphorylcholine group easily.

Furthermore, it is possible to introduce a phosphorylcholine group with very low adsorption of a protein or polypeptide into an object surface conveniently and quantitatively without damaging its fine structure. Moreover, no unreacted functional group except a phosphorylcholine group is introduced, and therefore, it is also possible to provide a raw material with very high biocompatibility. Moreover, it is also possible to use an amine group-containing phosphorylcholine compound according to the present invention as a starting material of another phosphorylcholine group-containing compound.

A substance or raw material modified by a surface-modifying agent including a phosphorylcholine group-containing compound according to an embodiment of the present invention is a material excellent in biocompatibility and hydrophilic property and a molded article therefrom. It is a matter of course that the material which directly has a phosphorylcholine group on the surface of a raw material and has biocompatibility is applicable to a wide variety of uses, such as for cosmetic materials, medical materials such as artificial organs and tools for surgical operation, packing materials for chromatography, affinity particles, and coatings.

Although the preferred embodiments and practical examples of the present invention have been described in detail above, the present invention is not limited to such particular embodiments and practical examples and it is possible to apply various alterations and modifications to these embodiments and practical examples without departing from the spirit and scope of the present invention.

The present application claims the benefit of its priority based on Japanese Patent Application No. 2007-009482 filed on Jan. 18, 2007, the entire contents of which are hereby incorporated by reference.

What is claimed is:

1. A method of manufacturing a phosphorylcholine group-containing compound represented by the following formula 2

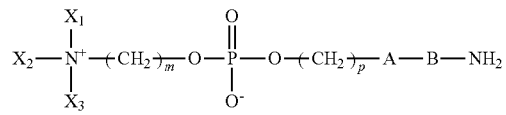

(Formula 2)

(in the formula, m is 2 or more and 6 or less and p is 1 or 2; each of X1, X2 and X3 is an alkyl group whose carbon number is 1 or more and 6 or less; A is an ester linkage or an amide linkage; and B is an alkylene group or a polyoxyethylene group), wherein the phosphorylcholine group-containing compound in the manufacturing method is synthesized by means of an oxidative cleavage reaction of glycerophosphorylcholine to synthesize a phosphorylcholine derivative having a carboxyl group and a condensation reaction of a compound having an amino group and the phosphorylcholine derivative having a carboxyl group.

* * * * *